(12) United States Patent
Sasaki

(10) Patent No.: US 7,481,768 B2
(45) Date of Patent: Jan. 27, 2009

(54) ULTRASONOGRAPH

(75) Inventor: Akira Sasaki, Chiba (JP)

(73) Assignee: Hitachi Medical Corporation, Ichikawa-shi (JP)

( * ) Notice: Subject to any disclaimer, the term of this patent is extended or adjusted under 35 U.S.C. 154(b) by 204 days.

(21) Appl. No.: 10/559,081

(22) PCT Filed: Jun. 1, 2004

(86) PCT No.: PCT/JP2004/007513
§ 371 (c)(1),
(2), (4) Date: Dec. 2, 2005

(87) PCT Pub. No.: WO2004/107981
PCT Pub. Date: Dec. 16, 2004

(65) Prior Publication Data
US 2006/0173308 A1 Aug. 3, 2006

(30) Foreign Application Priority Data
Jun. 3, 2003 (JP) ............................ 2003-157894

(51) Int. Cl.
*A61B 8/00* (2006.01)
(52) U.S. Cl. ..................... 600/443; 600/437
(58) Field of Classification Search ................. 600/437, 600/440, 441, 443
See application file for complete search history.

(56) References Cited

U.S. PATENT DOCUMENTS

| | | | | |
|---|---|---|---|---|
| 5,456,255 A * | 10/1995 | Abe et al. | ..................... | 600/443 |
| 5,993,392 A * | 11/1999 | Roundhill et al. | ........... | 600/447 |
| 6,258,033 B1 * | 7/2001 | Grenon | ........................ | 600/458 |
| 6,379,306 B1 * | 4/2002 | Washburn et al. | ........... | 600/454 |
| 6,666,824 B2 * | 12/2003 | Rust et al. | ................... | 600/443 |
| 6,749,569 B1 * | 6/2004 | Pellegretti | .................... | 600/441 |
| 6,896,658 B2 * | 5/2005 | Ji et al. | ........................ | 600/440 |
| 7,060,032 B2 * | 6/2006 | Sano et al. | .................. | 600/437 |
| 2003/0078497 A1 | 4/2003 | Ji | | |

FOREIGN PATENT DOCUMENTS

| | | |
|---|---|---|
| JP | 59-198315 | 11/1984 |
| JP | 1-141196 | 6/1989 |
| JP | 4-158854 | 6/1992 |
| JP | 7-241294 | 9/1995 |

OTHER PUBLICATIONS

Richard, William D., "A New Time-Gain Correction Method for Standard B-Mode Ultrasound Imaging", Sep. 1989, IEEE Transactions on Medical Imaging, vol. 8, No. 3, pp. 283-285.*

* cited by examiner

*Primary Examiner*—Eric F. Winakur
*Assistant Examiner*—Katherine L Fernandez
(74) *Attorney, Agent, or Firm*—Antonelli, Terry, Stout & Kraus, LLP.

(57) ABSTRACT

A probe 10 receives an echo signal, and the echo signal is stored in memory 18. Operation desk 28*a* has at least one readout-range setting device 34 for setting an echo signal readout-sensitivity range of the echo signal stored in memory 18. Echo signals in the sensitivity range preset by readout-range setting device 34 is read out from memory 18 from among the echo signals in the sensitivity range stored in memory 18. The echo signal read out of memory 18 is converted into data corresponding to the display dynamic range of monitor 24*a* by a digital gain regulation circuit 31. The converted data is inputted into image construction unit 22 to create image data. The image data is displayed on the screen of monitor 24*a*.

23 Claims, 13 Drawing Sheets

FIG. 10
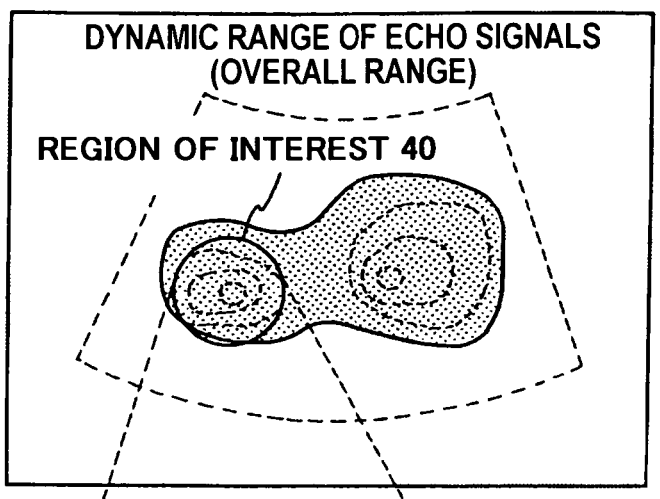
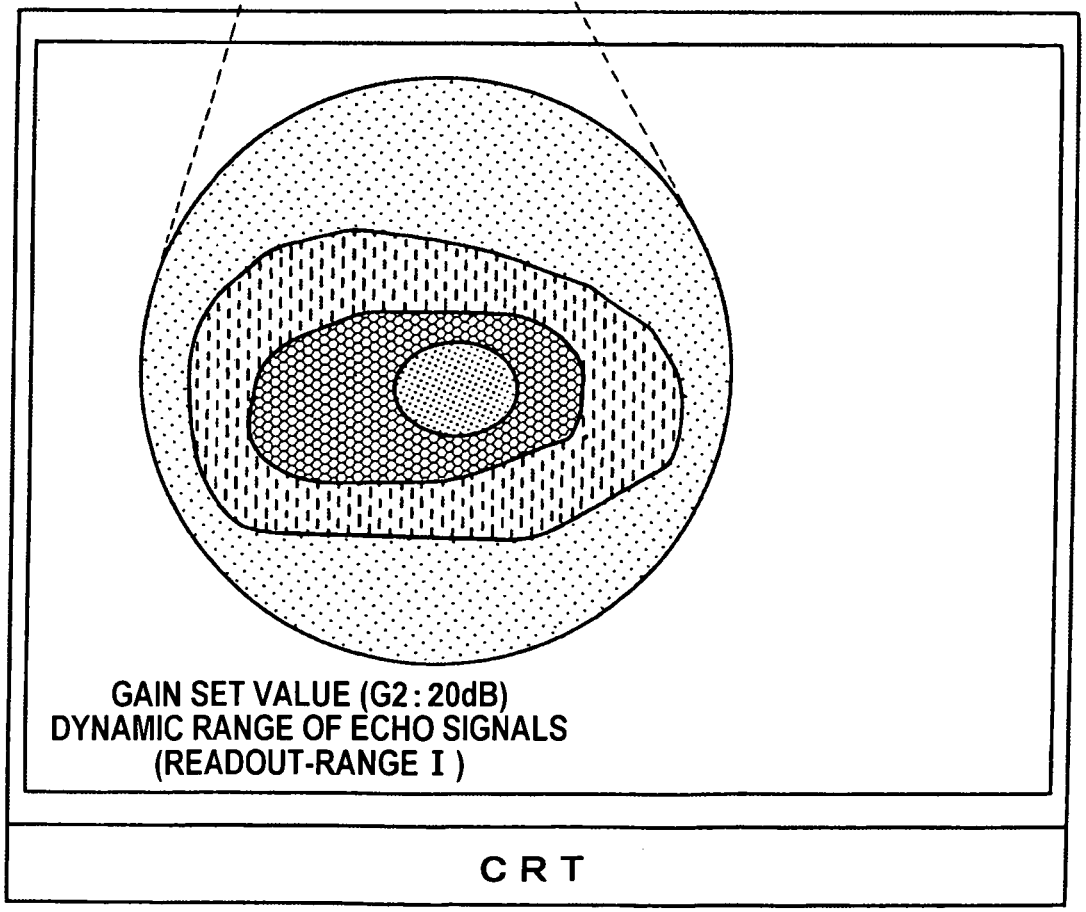

ULTRASONOGRAPH

TECHNICAL FIELD

The present invention relates to an ultrasonic diagnostic apparatus and in particular to the apparatus that is advantageous for observing the fine structure of a diagnostic region with the image in an optimal contrast resolution.

BACKGROUND OF THE INVENTION

An ultrasonic apparatus is an apparatus that transmits ultrasonic waves from a probe to the body surface of an object to be examined, electrically prosesses an echo reflected from the object, forms an ultrasound image (such as B-mode image, M-mode image, D-mode image, or CFM-mode image) from the processed echo signals, and displays the ultrasound images thereof on a monitor.

In such ultrasonic diagnostic apparatus, while a dynamic range that is a sensitivity range generally possible to be displayed on a monitor range is, for instance, between 0 dB~40 dB, there are cases that the dynamic range of the echo ranges is, for instance, between 0 dB~90 dB. In this case, when an ultrasound image is displayed on a monitor, there is a need to compress a dynamic ranges of an echo signals.

The difference in signal intensity of the echo signals derived from respective portions in the body organ structure such as a tumor of the liver, gall bladder and diaphragm are relatively small, thus the brightness difference are also small among the pixels that are forming ultrasound images of said organs, which often makes it difficult for the doctors to determine the fine structure of such diagnostic portions upon attempting ultrasonic diagnosis.

Given this factor, a sensitivity graded tomography that repeats the operation a number of times to obtain ultrasound images while changing the sensitivity of the acquired echo signals, and that observes the fine structure by comparing diagnostic portions by the plurality of ultrasound images of different sensitivity, had been conventionally suggested and clinically implemented. This sensitivity graded tomography is described, for example, in [nonpatent document 1].

Nonpatent document 1: The Japan Society of Ultrasonic in Medicine "Ultrasonic Diagnosis", published by Igaku-Shoin Ltd., in Jul. 15, 1994, p. 398 and p. 887 of first printing of the second edition.

Meanwhile, in the case of displaying ultrasound images by compressing the dynamic range of echo signals such as in the conventional ultrasonic diagnostic apparatus, since there is a possibility that the structures which derive the echo signals of close sensitivity would have the same level of clarity on the screen, it is difficult for the doctors in diagnosing the affected area of the image displayed because of the unobservable difference in clarity level.

In the above-mentioned conventional sensitivity graded tomography, it is necessary to repeat the operations many times to obtain the ultrasound images from an examined portion, and freeze the images obtained on the monitor and to shoot the photographs while changing the overall sensitivity range of the echo signals. Hence it takes much time and energy to obtain the plurality of ultrasound images that have different sensitivity, causing the problem of not being able to execute an efficient diagnose. Also, with conventional sensitivity graded tomography, since the overall sensitivity range of the obtained echo signals had to be displayed to a display dynamic range (display gradation sequence) on the monitor by compressing the range, differentiating echo signals with close sensitivity came along with difficulties.

Moreover, when doctors implement said sensitivity grading tomography, there is a need to change the sensitivity of obtained echo signals, so that the artifacts caused by the side lobe or grating lobe and so forth would not be actualized on the ultrasound images. Thus using said sensitivity grading tomography leaves a problem that the doctors are required to have advanced technique for regulating the apparatus.

The first objective of the present invention is to provide an ultrasonic diagnostic apparatus that makes it possible to observe anatomical features wherein the level of the echo signals are in a narrow range with clear images.

The second objective of the present invention is to provide an ultrasonic diagnostic apparatus that makes it possible to efficiently observe anatomical features wherein the level of echo signals are in a narrow range.

The third objective of the present invention is to provide an ultrasonic diagnostic apparatus that makes it possible to observe anatomical features wherein the level of the echo signals are in a narrow range without requiring doctors to have an advanced technique for regulating the apparatus.

DISCLOSURE OF THE INVENTION

In order to solve the above-mentioned problems, the present invention provides an ultrasonic diagnostic apparatus comprising:

a probe that transmits ultrasonic waves to the body of an object to be examined and receives the echo from the body of the object;

a reception unit that receives the echo signals from the probe;

a memory that stores the received echo signals at least a quantum of one image;

a means for reading out one image of a signal on each sensitivity range wherein the signal has a plural and different sensitivity range from the echo signals stored in said memory; and a means for converting and outputting said read out signals into the dynamic range of the monitor with respect to each sensitivity range.

The present invention was implemented, taking into consideration that if the echo signals are converted into digital signals and stored in the memory, the data of predetermined bits can be read out the echo signals. In other words, by discretionally setting the bit range (sensitivity range) of the read out echo signals with variability, it is possible to reconstruct the ultrasound images using the reflected echo signals of the necessary sensitivity range. Therefore by reading out the plurality of data of sensitivity range, it is possible to display the plurality of images by different sensitivity range on the monitor. By doing so it is possible not only to improve the compressibility ratio for displaying the ultrasound images on the monitor, but also to improve the image quality of displayed ultrasound images on the monitor, since it enables the display of image data and the dynamic range of the monitor to correspond with each other on a one-to-one basis by leveling out the readout-range to the dynamic range.

For example, if a reflected echo signal from an AD converter is 16 bits long, and the dynamic range of a reflected echo signals that is stored in a memory is 0 dB~96 dB, if the sensitivity range of the reflected echo signal read out from the memory is set as, for example, 40 dB~80 dB, 20 dB~60 dB, 0 dB~40 dB, the images can be displayed on the monitor with 0 dB~40 dB of dynamic range without compressing the dynamic range of the reflected echo signals read out from the memory.

In this case, when a region of interest is set as a region for an observation, it is possible to read out the reflected echo signals corresponding to the region of interest from the memory and display the ultrasound images on the monitor. By doing so it is possible to improve the display frame rate of the ultrasound images, because only the reflected echo signals that corresponds to the region of interest are read out.

In the present invention, it is possible to reconstruct various ultrasound images with different sensitivity range by obtaining only one frame of the ultrasound images and storing the echo signals in the memory. Thus compared to conventional sensitivity grading tomography that repeats the operation for obtaining ultrasound images and shooting frames, it is possible to shorten the time for obtaining the ultrasound images. Also, because it enables easy regulation of the sensitivity range of the reflected echo signals read out from the memory in order to avoid the actualization of artifacts and so forth on the ultrasound images, it is possible to simplify the operation to obtain adequate ultrasound images for diagnosis.

In this case, in order to obtain the ultrasound images in which the sensitivity range varies gradually, it is preferable to vary the sensitivity range to make the width of the range to be constant and the average sensitivity range to be different. By doing so, it is possible to obtain various ultrasound images with different sensitivity range, and the various ultrasound images thereof would gradually project the fine structure of a diagnostic area.

Moreover, in order to facilitate comparative observation on the plurality of ultrasound images, it is possible to display the plurality of ultrasound images with different sensitivity range on the same screen at the same time. For example, it makes it possible to arrange the plurality of ultrasound images with different sensitivity range and display them on the monitor at the same time, or to superimpose the translucent ultrasound images with changed hue information over other ultrasound images and display them on the monitor. By doing so the examiner is able to execute comparative observation, without moving the eyes, to perform more precise diagnosis.

Moreover, in order to display the plurality of ultrasound images with different sensitivity range relating to the region of interest, when an input means to set the region of interest is provided on the displayed ultrasound images and the region of interest is set by the input means, it is possible to read out the reflected echo signals with different sensitivity range in the region of interest and to display the ultrasound images with different sensitivity range on the monitor. With this feature, it is possible to determine the fine structure of the region of interest precisely, as well as to improve the display frame rate of the ultrasound images.

Moreover, it is possible to display not only B-mode images, but also M-mode images. By this feature, for example, in the case of not being able to identify the blocked blood vessel in the endosporium of left ventricle being buried by the pedicardia fat, by changing the sensitivity range of M-mode images displayed on the monitor in phase according to the measurement time, the blocked blood vessel will be projected gradually, so that the clog can be identified.

Further, in the present invention, it is possible for B-mode images with different sensitivity range and M-mode images with different sensitivity range to be arranged in order and displayed at the same time. With this advantage, it is possible to determine the fine structure of the diagnostic portion (diaphragm, for example) by B-mode images, and to measure the temporal response of the embodiment toward the beam direction of the diagnostic portion by M-mode images at the same time.

BRIEF DESCRIPTION OF THE DRAWINGS

FIG. 10 is a diagram showing one display mode for displaying the original images and the images with different dynamic range at the same time.

BEST MODES FOR CARRYING OUR THE INVENTION

Embodiment 1

Figure 1:
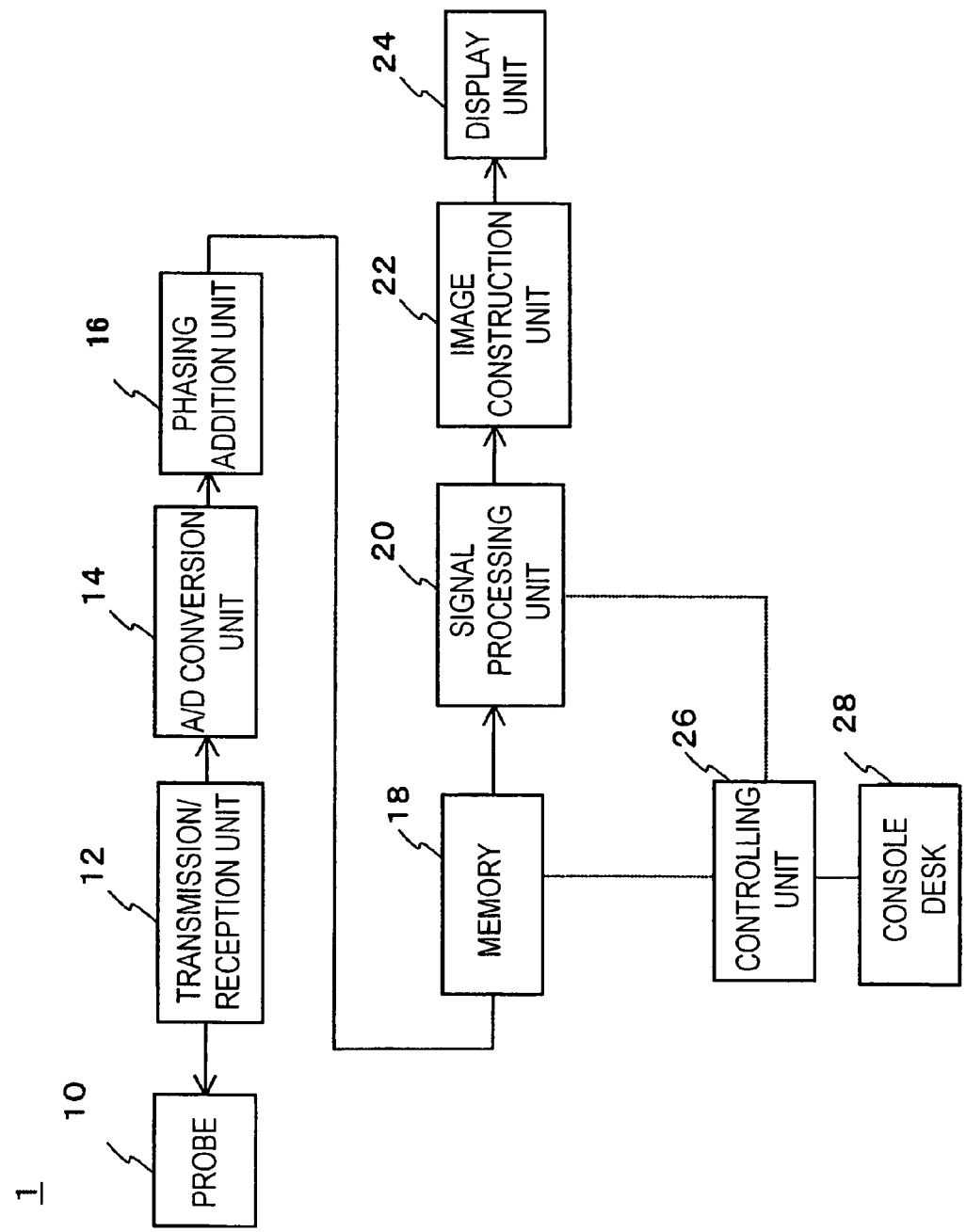
FIG. 1 is a block diagram showing the schematic configuration of the ultrasonic diagnostic apparatus relating to the present invention.

The first embodiment of an ultrasonic diagnostic apparatus relating to the present invention will now be described referring to FIG. 1 to FIG. 8. First, the configuration of the ultrasonic diagnostic apparatus relating to the present invention will be described using FIG. 1 and FIG. 2.

Ultrasonic diagnostic apparatus 1 is configured of probe 10, transmission/reception unit 12 that has a transmission unit and a reception unit, AD conversion unit 14, phasing addition unit 16, memory 18, signal processing unit 20, image construction unit 22, display unit 24 that has a monitor, controlling unit (CPU) 26, console desk 28, and so forth.

Next, the operation of the above-mentioned ultrasonic diagnostic apparatus 1 will be explained. First, a doctor applies probe 10 on the body surface of an object to be examined. Next, the doctor inputs an order to start ultrasound examination using console desk 28. Corresponding to a starting order, an order to output driving pulse is issued by CPU 26 to the transmission unit of transmission/reception unit 12. The outputted driving pulse is delivered to the arrayed transducer placed in probe 10, and ultrasonic waves are transmitted to the object from probe 10. In addition, the known transmission focusing technique is used for the ultrasonic waves transmitted from the arrayed transducer of probe 10 to the object, to be converged in predetermined depth of the body of the object.

The reflection waves (echo) generated from the body of the subject are received by arrayed transducer of probe 10. The above-mentioned transmission/reception operation of ultrasonic waves is repeatedly performed in a predetermined cycle, changing the direction for transmission/reception. Echo signals that received by probe 10 are converted from sound signals into electronic signals (echo signals) by respective transducers. Echo signals from respective arrayed transducers are converted into digital signals (for example, digital signals of 16 bits long) by AD converting unit 14.

The respective echo signals converted into digital signals are inputted to digital phasing addition unit 16. Digital phasing addition unit 16 is comprised of: a digital phasing circuit consists of the channels that are two times in number of the arrayed transducer which contributed to the reception of echo signals; and two adding circuits. The reception focusing process is executed by this digital phasing addition unit 16. The reception beam signals of complex signals are outputted from digital phasing addition unit 16 by the above reception focusing process. The explanation on the configuration of digital phasing addition unit 16 which exercises phasing addition of digital echo signals will be omitted here, since it is well known as a digital phasing technique in various documents.

After the phasing of the respective echo signals are phased at digital phasing addition unit 16, the real part and the imaginary part of the complex reception beam signals that are outputted from digital phasing addition unit 16 are stored in memory 18. Memory 18 consists of Q memory which stores the real part of the complex reception beam signals and a memory which stores the imaginary part of the same, and the real part and the imaginary part which consist the reception beam signals are separated and stored to each of said memories. The echo signals stored in memory 18 are read out according to the order from CPU 26, and then the detection, logarithmic compression and so forth are implemented in signal processing unit 20. The echo signals outputted from signal processing unit 20 are then formed as ultrasound image data which are, for example, B-mode image data, in the frame memory of image construction unit 22, and the B-mode images are read out by scanning conversion method and are displayed as B-mode images on the monitor of display unit 24.

Figure 2:
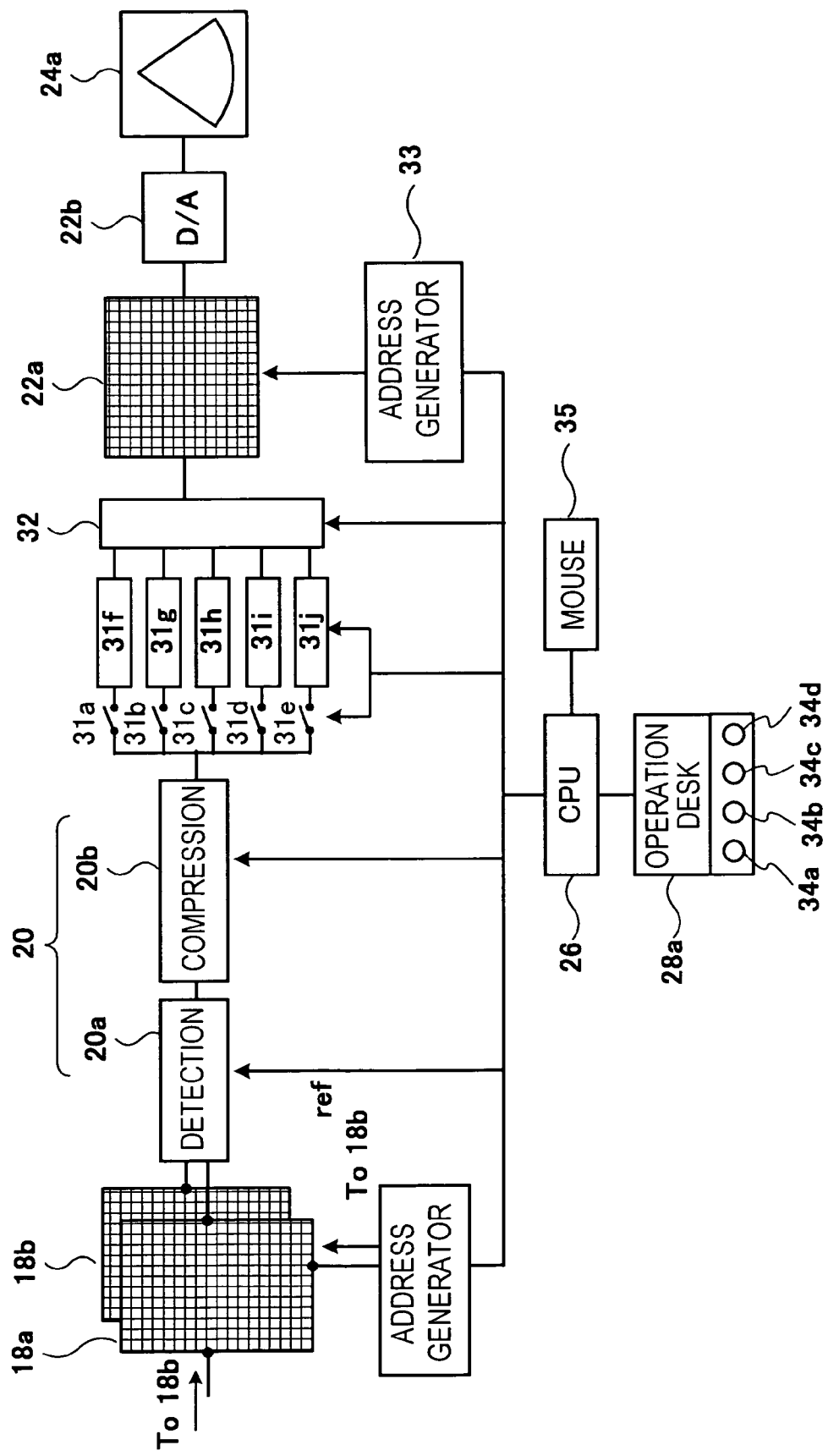
FIG. 2 is a block diagram showing the main part that forms and displays the plurality of images with different sensitivity range.

Next, in order to solve the above-described problems, the sections that characterize the present invention will now be described in details. FIG. 2 is a diagram showing the circuit configuration that performs the signal processing after memory 18, which is a part of the device configuration shown in FIG. 1. In FIG. 2 as described above, memory 18 consists of memory 18a that stores the real part of the echo signals and memory 18b that stores the imaginary part of it. The address signals that designate writing or readout-address of the echo signals to said memory 18a and 18b are outputted from address generator 30 controlled by CPU 26 to memory 18a and 18b. To subsequent part of memory 18a and 18b, signal processing 20 including quadrature detection circuit 20a and compression circuit 20b is connected, and two signals consist of the real part and the imaginary part stored in memory 18 are composed in quadrature detection circuit 20a, and converted into one echo signal for forming images, and outputted.

Digital gain regulation circuit 31 that converts data of dynamic range of echo signals outputted from signal processing unit 20 into displayed dynamic range on the monitor of displaying unit 24 is connected to subsequent part of signal processing unit 20. Digital gain regulation circuit 31 has the same number of digital gain regulation circuits as the images to display on the monitor. For example, in the case of displaying four images of different dynamic range, it has four digital gain regulation circuits. The respective digital gain regulation circuits are comprised of a switch to implement on/off input of the signals and digital gain regulator. More specifically, four digital gain regulation circuits are provided, each comprised of switch 31a and digital gain regulator 31f, switch 31b and digital gain regulator 31g, switch 31c and digital gain regulator 31h, switch 31d and digital gain regulator 31i, and switch 31e and digital gain regulator 31j.

The output signals of the digital gain regulation circuit 31 are outputted to image construction unit 22 via signal switching device 32. Signal switching device 32 has a changeover switch (diagrammatic presentation is omitted) in each spacing between outputting line of digital gain regulators 31f, 31g, 31h, 31i and the outputting line of signal switching device 32. On/off timing of the above switches is controlled by orders from CPU 26. And the number of images to display on the monitor of displaying unit 24 can be set up to switchover by appropriately programming the on/off controlling of said changeover switches by CPU 26.

Image construction unit 22 is referred to as Digital Scan Converter (DSC) in the field of ultrasonic diagnostic apparatus, and converts the scanning of ultrasonic waves and the scanning of the image display. To accomplish said conversion, image construction unit 22a has frame memory 22a. The echo signals inputted to image construction unit 22 are sequentially written in the writing address which is outputted from an address generator 33 controlled by CPU 26 to frame memory 22a, and by said process the ultrasound images are formed in frame memory 22a. The ultrasound image data formed in frame memory 22a are synchronized with display scanning of the monitor and are read out as line data of crossed direction to the writing direction of the echo signals. The readout address of this reading-out process is outputted from said address generator 33.

When at least one ultrasound scanning is completed, the image data loaded in memory 18 is outputted from image construction unit 22, converted into brightness signals by A/D converter 22b, inputted to monitor 24a of display unit 24, and displayed as ultrasound images.

It is preferable that the image data loaded in memory 18 are the ones that project the object region of examination at its best, because they are used to form the plurality of images with different sensitivity range afterwards. Therefore it is desirable for the operators to observe and probe the ultrasound images displayed in real time on monitor 24a, and to freeze the image that projects the object region of the examination at its best.

Figure 3:
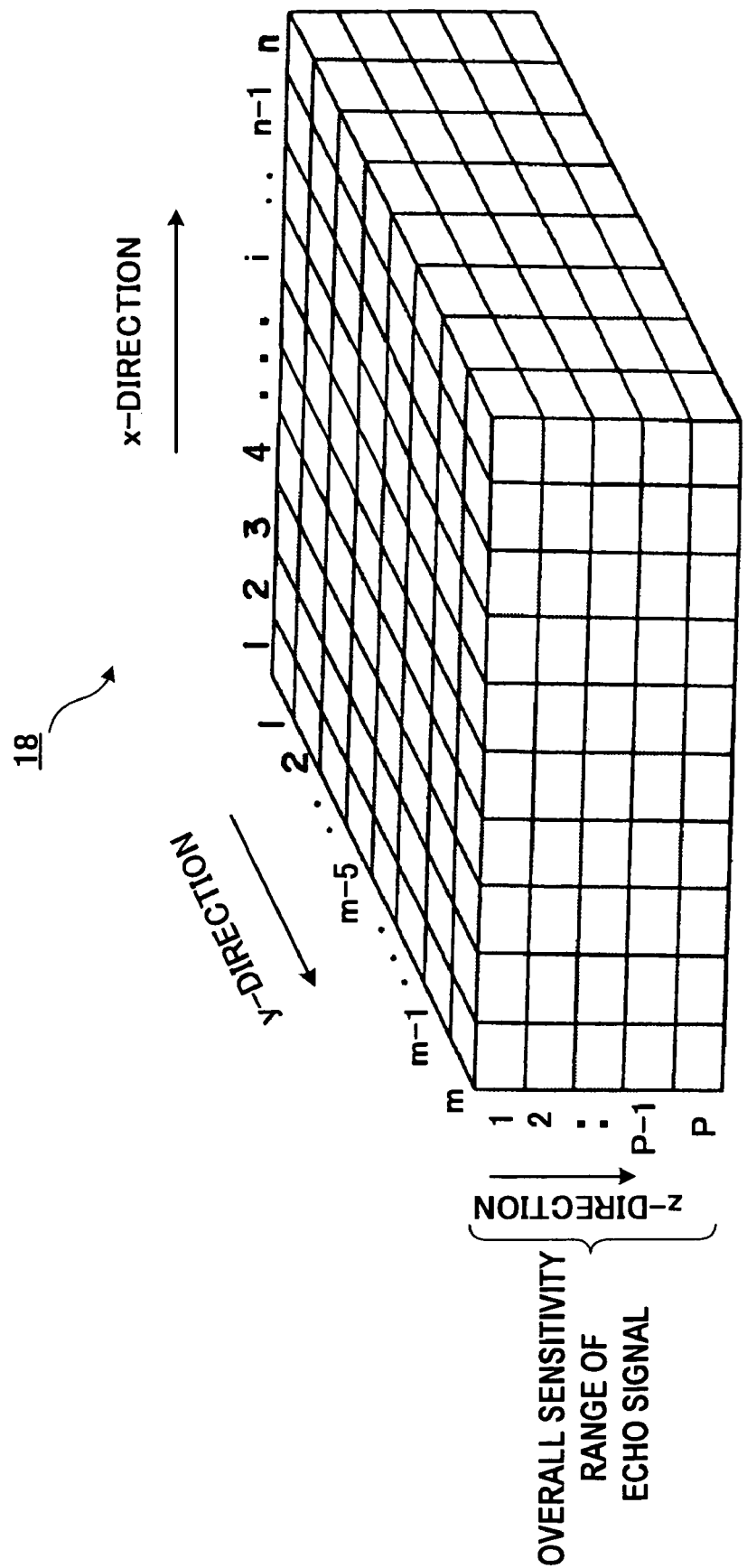
FIG. 3 is a schematic diagram of a memory that stores the echo signals by sensitivity.

Next, the embodiment related to reading out the echo signals of a given number (more than one) of images that have predetermined sensitivity range (dynamic range), and for displaying those images by displaying dynamic range in monitor 24a will now be described. FIG. 3 conceptually indicates memory 18 and the echo signals stored therein. Also, memory 18 will be explained with representation of one memory even though it is comprised of memory 18a for the real part and memory 18b for the imaginary part as shown in FIG. 2.

The echo signals (reception beam signals) outputted from the digital phasing addition unit 16 are stored in the memory space of memory 18. This memory space is 3-dimensional memory space that consists of, for example, x-direction corresponding to the scanning direction of the ultrasound beams, y-direction corresponding to the depth direction, and z-direction corresponding to the gradation direction (sensitivity direction) of the echo signals. The memory area of Z-direction has 16 bits in order to store the overall gradation of the reception beam signals, for example, 0 dB~96 dB of dynamic range.

In memory 18, in the case of displaying only the real-time images obtained by scanning the ultrasound beams, it is sufficient to have the number of address arrayal in x-direction corresponding to the number of reception beams obtained in one transmission of ultrasound beam. However, since a freezing function of the images is required in ultrasonic diagnostic apparatuses, in this embodiment, memory 18 has the number of address arrayal equivalent to those of the reception beams in x-direction that form one ultrasound image. By this, the dynamic range of the displayed images can be altered, even in the state in which the transmission/reception of ultrasound has been halted, i.e. as when renewal of the images has been halted.

Figure 4:
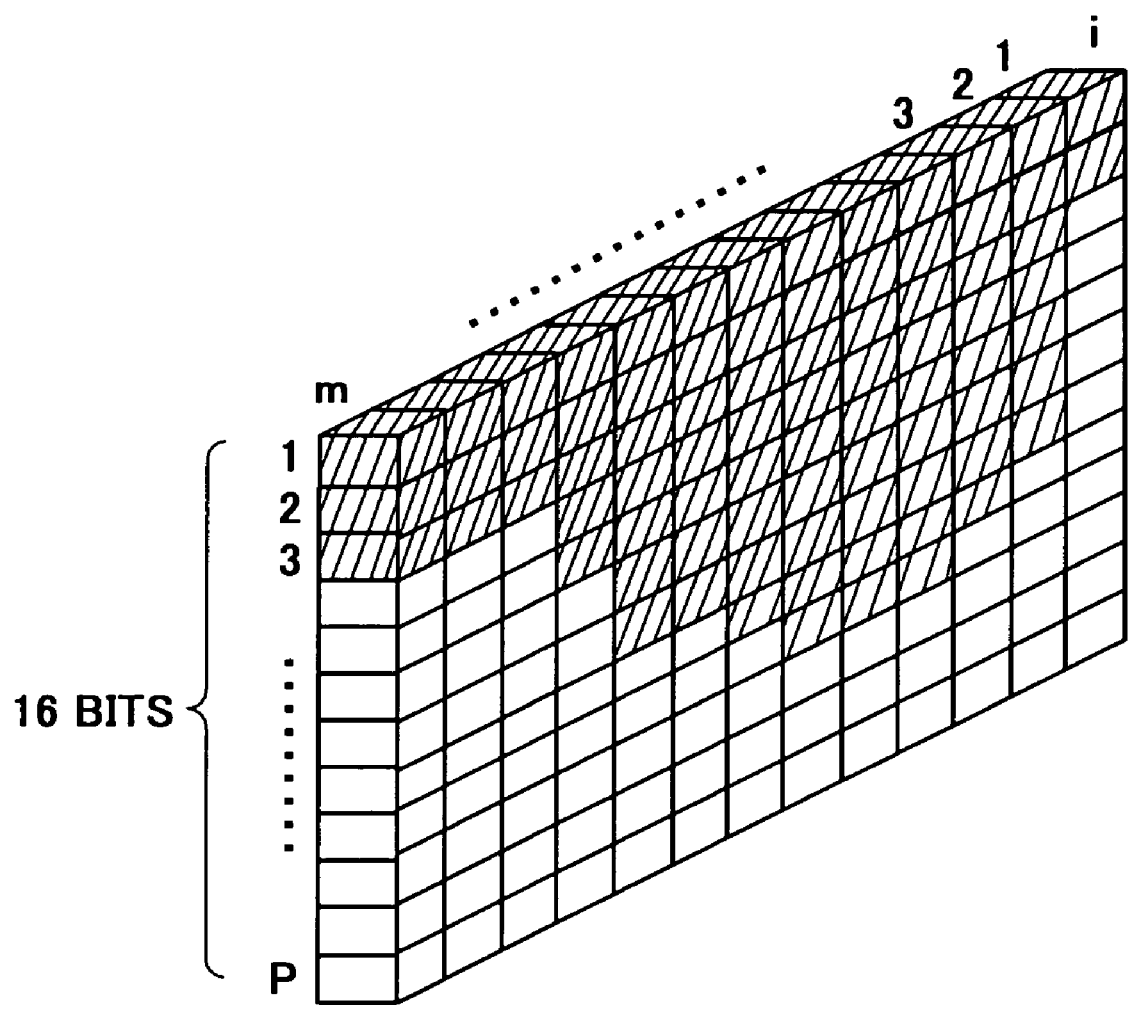
FIG. 4 is a diagram showing the memory condition of one reception beam to the memory shown in FIG. 3.

In FIG. 3, n indicates that the ultrasound images are formed by n number of reception beam signals, that the acquisition of the reception beam signals is implemented in sequence from 1 to n, and that one reception beam signal (i-th signal) is stored in memory 18 currently. FIG. 4 indicates the memory condition of the i-th reception beam signals in x-direction. In other words, i-th reception beam signals are provided with the address of "i" to the scanning direction, m-number of address out of 1~m are provided to the depth direction of the object, and to the strength direction (sensitivity direction) of the signal, the address as sort of histogram of 1~p of which p is the maximal value according to signal strength to the respective address of depth direction is provided. This signal strength of 1~p of which p is the maximal value is quantized to correspond to the dynamic range of, for example, 0 dB~96 dB.

The data loaded by ultrasound beam scanning to x-direction, y-direction and z-direction of memory 18 are read out by an order to read out the set range inputted by the operator to operation desk 28a. In order for the operator to input an order for setting the reading-out region, the plurality of readout range-setting device 34, for example, four of them (34a, 34b, 34c, and 34d) are provided in operation desk 28a (see FIG. 2). Reading-out range-setting device 34a, 34b, and 34c are connected, for example, to CPU 26, and are comprised of the circuits including the variable resister and a knob provided on operation desk 28. When the operator gives a desired rotation quantity to the knob, the output signals of the variable resister are variably set, and these output signals are inputted to CPU 26. CPU 26 sets up the midmost address of the set readout range to z-direction of memory 18 corresponding to the input signals, and outputs them to address generator 30. In this case, since the output signals are to determine the midmost address of the readout address range toward z-direction, readout range-setting device 34d is provided in operation desk 28a to set the vertical range for the midmost address. This readout range-setting device 34d has the same configuration as the other setting devices 34a, 34b, and 34c, and CPU 26 in which the output signals of readout range-setting device 34d is inputted to set the vertical range for the midmost address with a software-like process.

Figure 5:
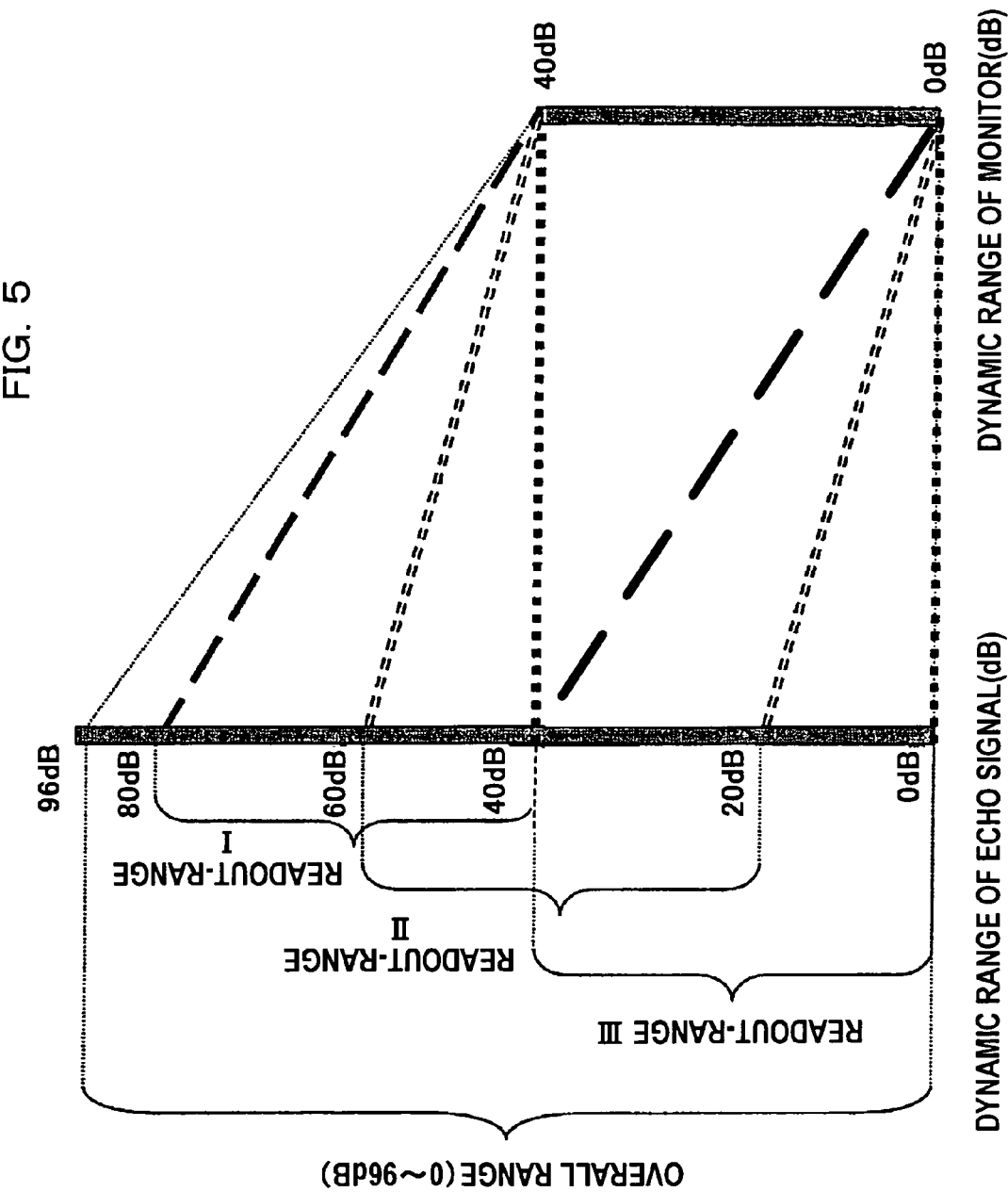
FIG. 5 is a schematic diagram showing the first embodiment of the data conversion for displaying the echo signals stored in the memory.

Here we make the assumption that, for example, the midmost address 60 dB, 40 dB, and 20 dB and the address range 40 dB (the vertical range for the midmost address is 20 dB) are set in readout range-setting device 34. When the above-like setting is implemented, as to the echo signals stored in memory 18, as shown in FIG. 5 as one embodiment of display, the echo signals of 40 dB~80 dB, the echo signals of 20~60 dB, as well as 0~40 dB are respectively converted into the display dynamic range of 0~40 dB of monitor 24a and displayed. More specifically, among the echo signals stored in memory 18, those of 80 dB are as 40 dB, those of 60 dB are as 20 dB, and those of 40 dB are as 0 dB, displayed on monitor 24a.

Figure 6:
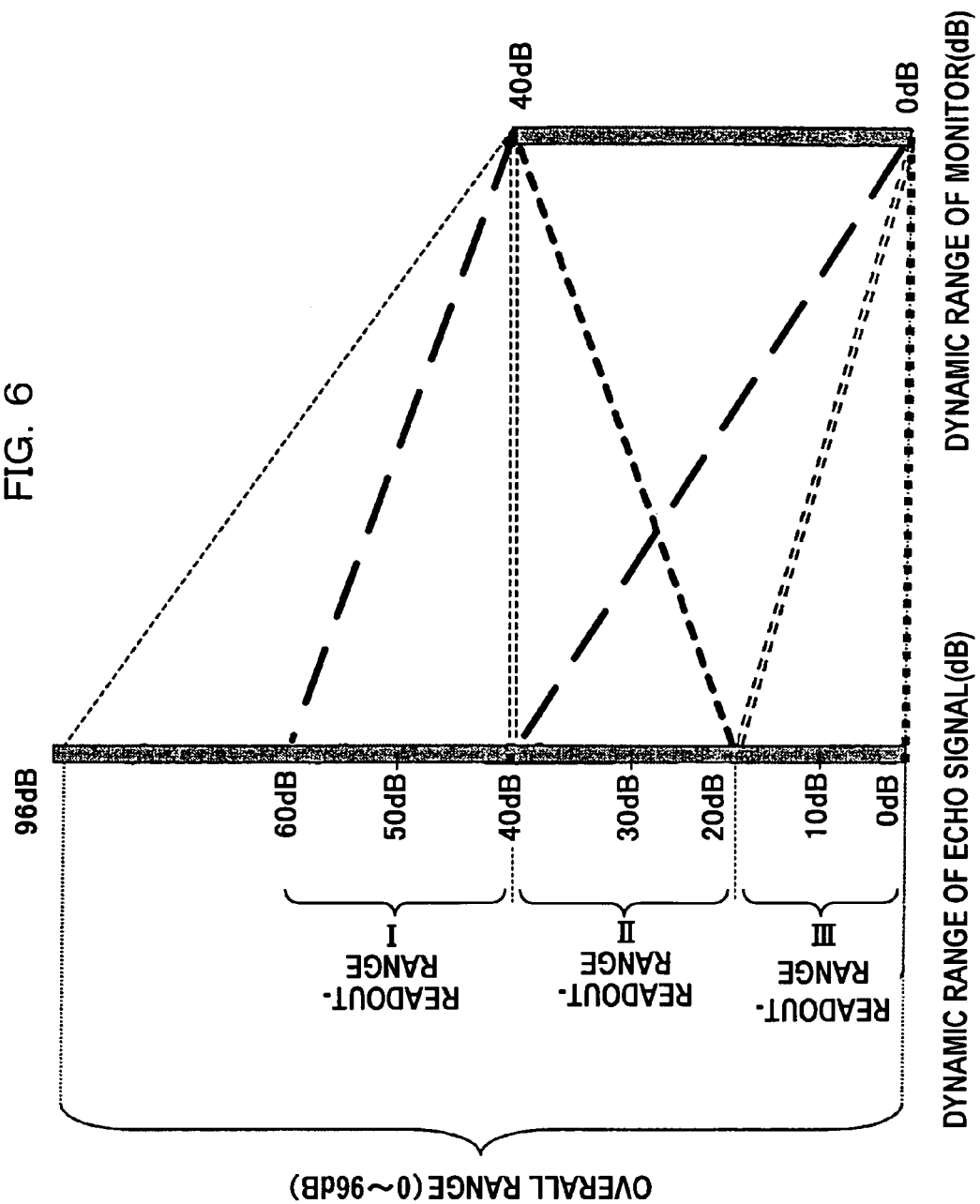
FIG. 6 is a schematic diagram showing the second embodiment of the data conversion for displaying the echo signals stored in the memory on the monitor.

Now we make the assumption of the case that the midmost address 50 dB, 30 dB, and 10 dB, and the address range 20 dB are set in readout range-setting device 34. When the above-like setting is implemented, as to the echo signals stored in 18, as shown in FIG. 6 as the other embodiment of display, echo signals of 40~60 dB, the echo signals of 20~40 dB, as well as the echo signals of 0~20 dB are respectively converted into the display dynamic range of 0~40 dB of monitor 24a and displayed.

In this way, according to the present embodiment, the echo signals with discretional dynamic range can be read out from the echo signals stored in memory 18 and displayed as an image. The different readout-echo signals, in relation, can be set so that a part of their dynamic range is overlapped, or not overlapped.

In this embodiment, the possible cases of setting at least one midmost address of 60 dB, 40 dB and 20 dB for readout range-setting devices 34a, 34b and 34c, and also the midmost address of 40 dB for readout range-setting device 34d are as follows:

(1) The case that the midmost address of 60 dB is set for one of readout range-setting device, for example, readout range-setting 34a, and the other readout range-setting devices 34b and 34c are turned off;

(2) The case that the midmost address of 60 dB, 40 dB and 20 dB are sequentially switched and set for readout range-setting device 34a, and the midmost addresses would not be set for other readout range-setting devices 34b and 34c;

(3) The case that the midmost address of 60 dB is set for readout range-setting device 34a, 40 dB is set for the device 34b, and 20 dB is set for the device 34c, and the midmost address would not be set for the remaining device 34d.

Figure 7:
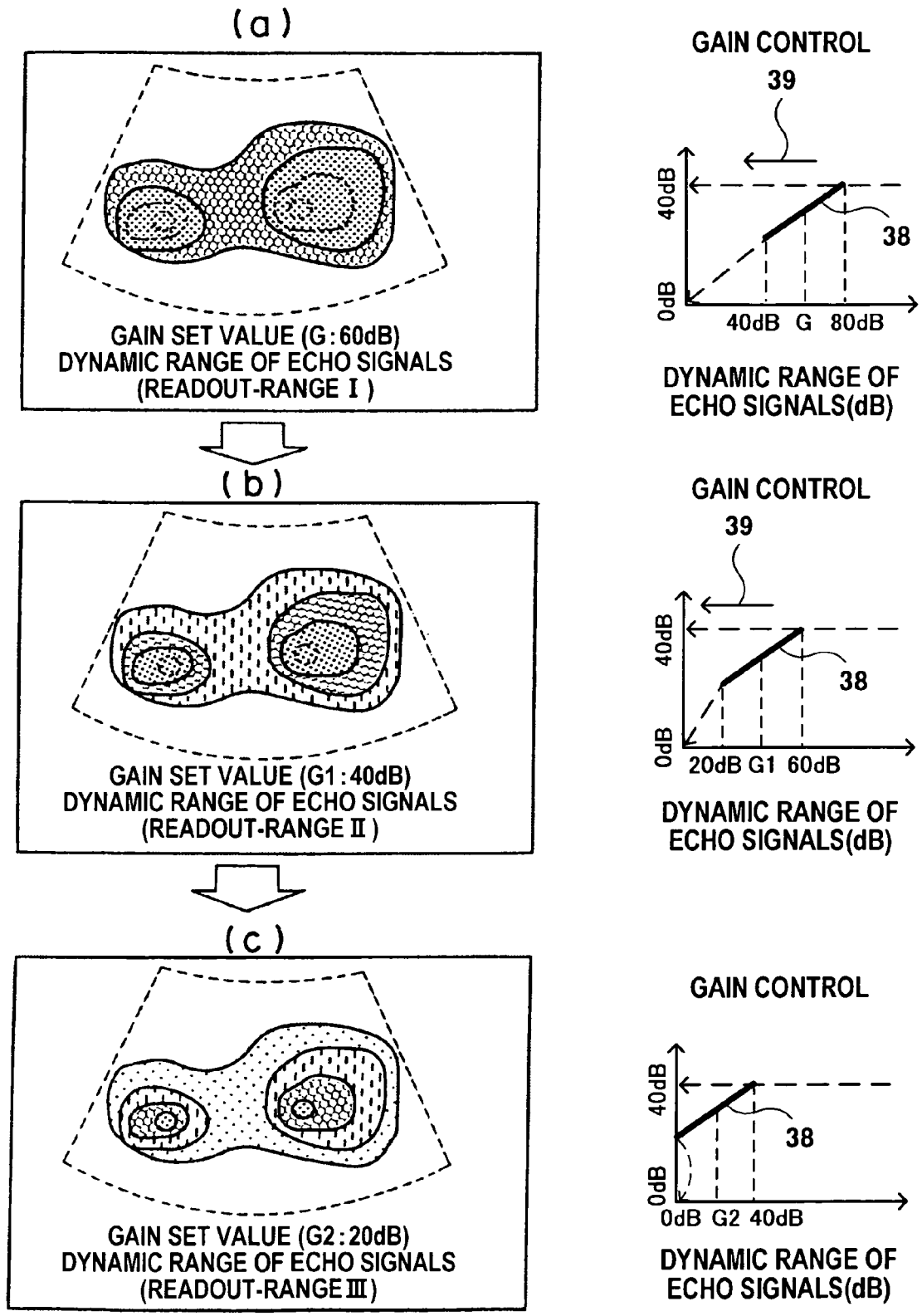
FIG. 7 is a diagram showing the display mode that displays the B-mode images with different dynamic range on the monitor in sequential order.

Out of the above-mentioned cases, cases (1) and (2) will now be described referring to FIG. 7. The left side of FIG. 7 shows the images displayed on the monitor, and the charts that indicate the relation between the dynamic range of the respective echo signals (horizontal axis) and the dynamic range of the monitor (vertical axis) are shown on the right side. The solid line of the chart indicates the data range that read out from memory 18.

In case (1), out of the measured ultrasound image data, the ultrasound image data with dynamic range (readout-range) of 40~80 dB (midmost G: 60 dB) are read out from memory 18. Out of the above readout data, those of 40 dB are displayed as 0 dB on the monitor, those of 80 dB are displayed as 40 dB on the monitor, and those of between 80 dB~40 dB are converted into the display dynamic range data of the monitor according to its dB and displayed. Then switch 31a and digital gain regulator 31e are operated by CPU 26. By this, the ultrasound image data of readout-range I are regulated and displayed by 0~40 dB dynamic range of the monitor (see FIG. 7a).

In case (2), following the same pattern as the above-mentioned case (1), the ultrasound image data of 20~60 dB (midmost G1:40 dB) dynamic range (readout-range II) are converted by digital gain regulator 31f and outputted, then regulated and displayed by 0~40 dB dynamic range of the monitor (see FIG. 7b). As a next step, the ultrasound image data of 0~40 dB (readout-range III) are converted into the data by digital gain regulator 31g and outputted, and displayed by 0~40 dB dynamic range (midmost G2:20 dB) of the monitor (see FIG. 7c). In other words, in case (2), individual ultrasound image with different dynamic range of measured ultrasound images is outputted via frame memory 22a, and displayed sequentially on the whole screen of the monitor.

Therefore in the cases of (1) and (2), it is possible to observe the effected area with high-definition images. Further, in case (2), the operator can implement the setting of readout-range I, II, and III prior to the launch, by operating readout range-setting device 34, or by observing the displayed ultrasound images on the monitor by operating readout range-setting device 34. It can also be implemented by installing software in CPU 26 that displays the image data of the same dynamic range by predetermined time or by predetermined number of the images sequentially and automatically to monitor 24a.

The contrast between the B-mode images of FIG. 7 (a)~(c) and the ordinary B-mode images will now be described. First, the ordinary B-mode images are based on the overall range of the echo signals obtained as a sensitivity range, thus the brightness difference among display pixels is small, making it difficult to determine the fine structure of a tumor of the liver. On the contrary, the B-mode images in FIG. 7(a) are based on the echo signals of readout-range I, thus in comparison with the ordinary B-mode images, the fine structure of a tumor of a liver, is vaguely projected. Furthermore, the B-mode images in FIG. 7(c) are based on the echo signals of readout-range III, thus in comparison with the B-mode images in FIG. 7(b), the fine structure of the a tumor of the liver is projected even more precisely. In this way, by displaying the B-mode image with different sensitivity range basing on the plural echo signals of different and set readout-range I~III and implementing comparative observation, the fine structure of the tumor of a liver, for example, can be precisely determined.

Figure 8:
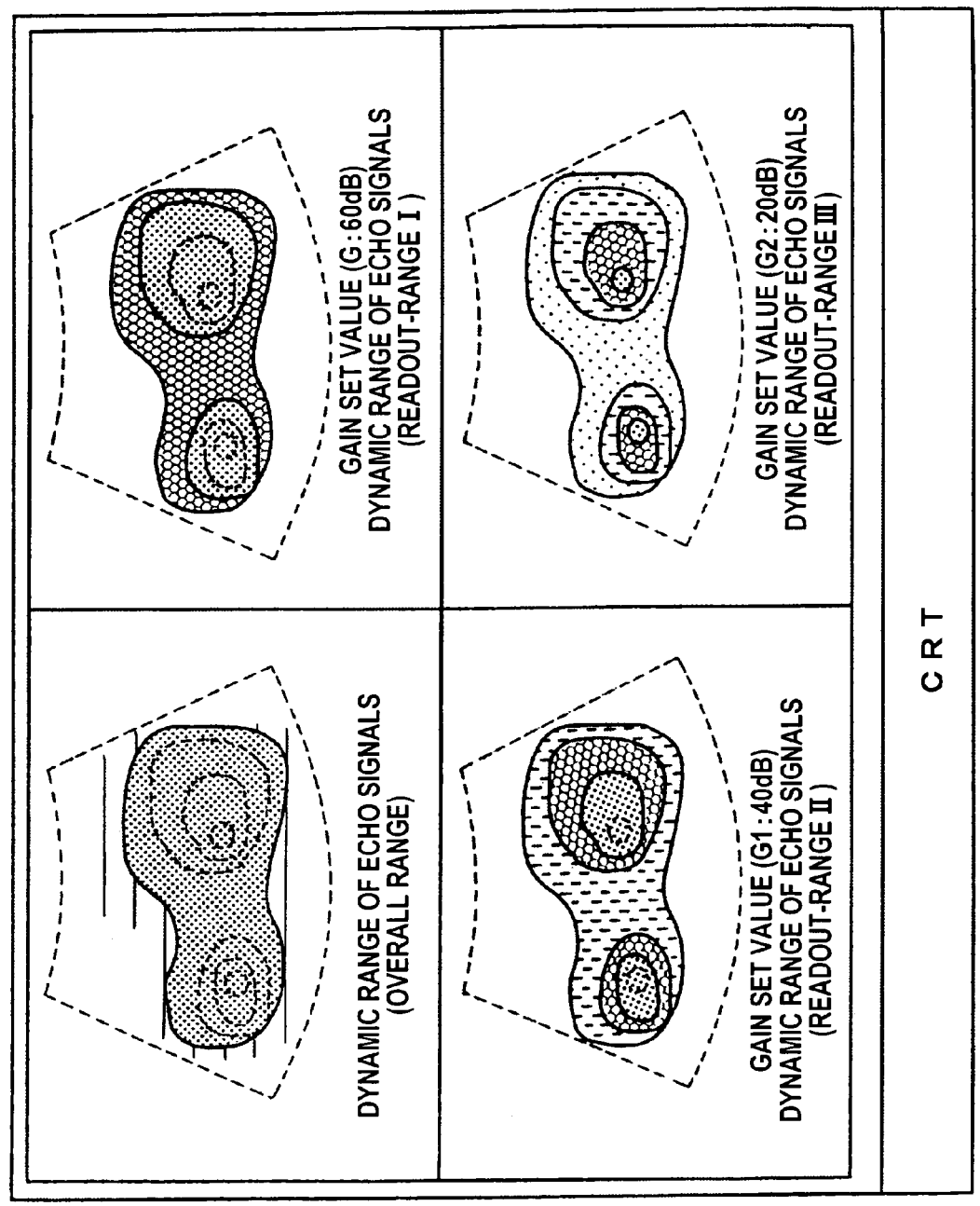
FIG. 8 is a diagram showing the embodiment for displaying the plurality of B-mode images with different dynamic range on the monitor simultaneously.

Moreover, in case (2), the ultrasound image data of 40~80 dB dynamic rage (readout-range I), the ultrasound image data of 20~60 dB dynamic range (readout-range II), and the ultrasound image data of 0~40 dB dynamic range (readout-range III) are displayed all at once on the screen that is segmented as seen in FIG. 8.

In this case, even though the preciseness of each image falls short for the above-mentioned cases (1) and (2), because it is possible to observe the image data of different dynamic range simultaneously, the effected area can be observed by comparing the different images on the same screen.

In addition, in case (2), there is one empty segment among four segments on the monitor, and the ultrasound image data of the measured and overall dynamic range can be displayed there.

In this case (2), the operation device to input the number of display images to operation desk 28a should be set up, and then by inputting "4" to the operation device, in the configuration of FIG. 2, all of the ultrasound image data covering the overall sensitivity range 0~96 dB stored in memory 18 should be read out, switch 31 should be turned on, then the output signals thereof should be inputted to digital gain regulator 31, converted into 0~40 dB dynamic range, outputted to signal switching device 32, and the empty segment on the monitor should be filled in through operating signal switching device 32 with predetermined order by the CPU. The result of the above-mentioned operation is shown in FIG. 8. In FIG. 8, the B-mode images by the ultrasound image data of the overall dynamic range are displayed on the upper-left region of the divided segments, the B-mode images by the ultrasound image data of 40~80 dB are displayed on the upper-right region, the B-mode images by the ultrasound image data of 20~60 dB are displayed on the lower-left region, and the B-mode image by the ultrasound image data of 0~40 dB are displayed on the lower-right region. The display position of those images would not be limited as the one shown in FIG. 8.

Figure 9:
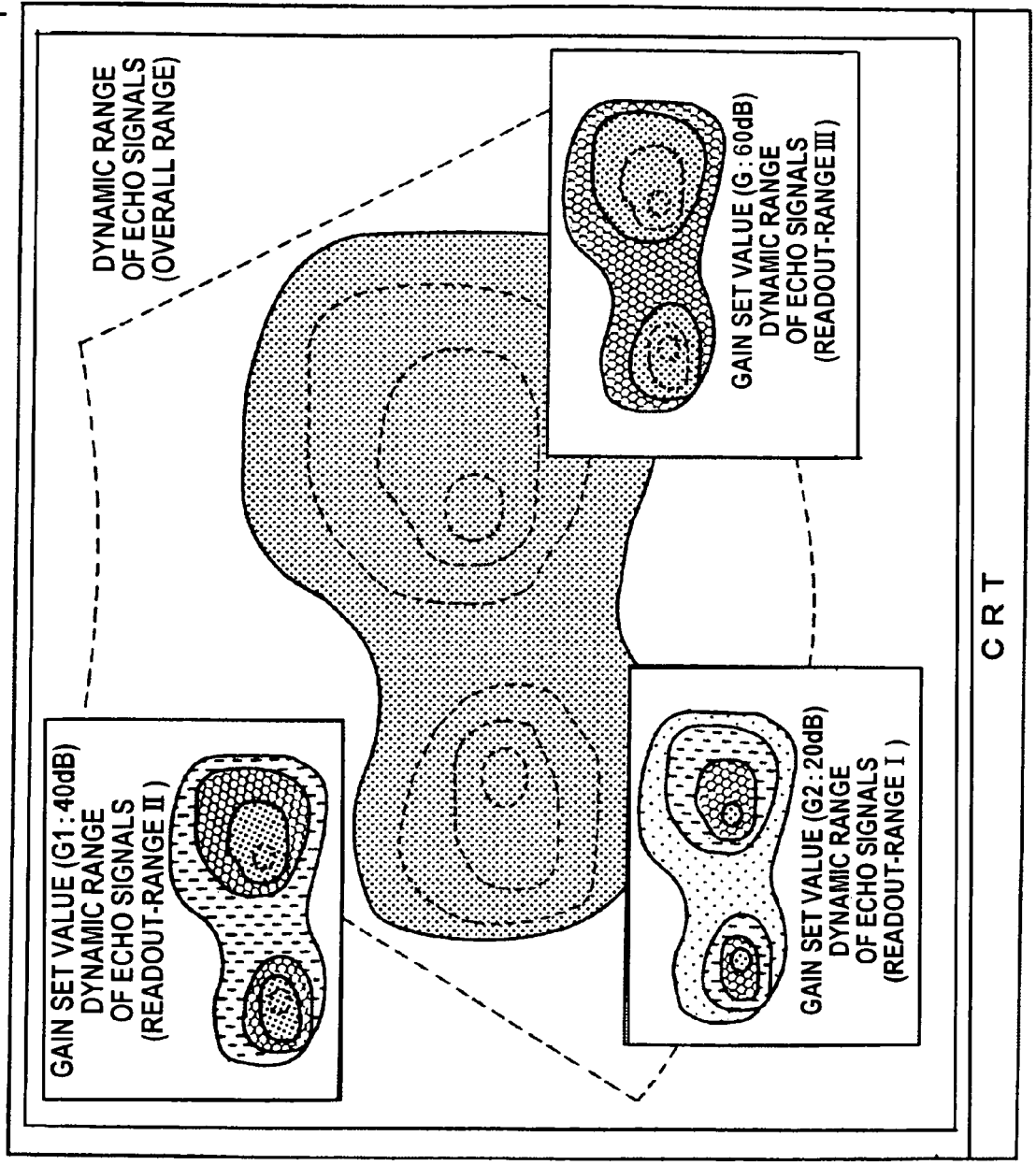
FIG. 9 is a diagram showing the embodiment for displaying the B-mode images with different dynamic range relating to the region of interest (RO).

Another example of case (2) for displaying the plurality of the B-mode images with different sensitivity range will now be described referring to FIG. 9. In FIG. 8, the example is displayed wherein the plural B-mode images with different sensitivity range are arranged on the same screen simultaneously. In FIG. 9, though, the example is displayed wherein the plural B-mode images with different sensitivity range are reconstructed, and the reconstructed respective B-mode images are reduced in size, then superposed over the original B-mode images and displayed. This sort of image-display is possible to be exercised using well-known image composing technique, thus the detailed explanation will be omitted.

As described above, by displaying the plural B-mode images with different sensitivity range simultaneously on the same screen, it is much easier to observe the plurality of the images by comparing them without changing eye position very much. The number of B-mode images to display simultaneously can also be set with variation.

The above cases (1)~(3) can be varied to the embodiment that the only region of 40 which the examinee desires to observe (region of interest: ROI) is imaged by the image data with different sensitivity range, and the created images are displayed on the monitor. In this embodiment, the region of interest 40 is set in the B-mode images displayed on the monitor using a positional information input device connected to CPU 26, for example, mouse 35 (see FIG. 10a), and when it is set, the echo signals of one or plural designated dynamic range corresponding to the region of interest 40 should be read out from memory 18 and displayed on the monitor. As for the region of interest, it is preferable to provide the following optional embodiments for the operator to be able to designate: the embodiment to compose with the original images except those of the region of interest to display on the monitor, or the embodiment to display only the region of interest (see FIG. 10b). Upon executing the latter embodiment of the above-mentioned options, it is possible to provide accurate examination since only the region of interest is displayed with high definition.

Said display means can be executed by controlling address generator 30 that reads out data from memory 18, readout range-setting device 34, digital gain regulator 31, and signal switching device 32 by CPU 26.

As mentioned above, in the present embodiment, it is possible to display with ease the plurality of ultrasound images with different sensitivity range by obtaining only one B-mode image which projects the portion of examination at its best and storing the obtained image to memory 18. Therefore comparing to conventional sensitivity graded tomographies that require repeating the operation to obtain B-mode images, it is possible to reduce the time for obtaining the images and for executing examinations.

Additionally, it will be easily understood by a person skilled in this art that the present invention can be carried out in the freeze mode of the above-mentioned B-mode images, or also in the case of searching the effected area while renewing the B-mode images in real time.

It also is possible for the present invention to simplify the operation to obtain pertinent B-mode images, since the sensitivity range of the reflected echo signals read out from memory 18 can be easily regulated so that the actualization of the artifact can be prevented on the B-mode images displayed on the monitor.

Moreover, in this embodiment, it can be arranged to vary the sensitivity range automatically. The previously mentioned arrangement can be carried out by preparing the software, so that the average sensitivity of the readout-range is set as reference gain set value G (60 dB, for example), and then, corresponding to this reference gain set value G, the automatic function is set for gain set value G1 (40 dB, for example) and gain set value G2 (20 dB, for example) that are to be automatically staggered by every step (for example, every 20 dB steps) as shown in FIG. 7. At this time, gain steps for setting the gain set value G1 and G2 corresponding to reference gain set value G can be set either by way of experiment or of experience.

The reference position for staggering the sensitivity range in incremental or decremental steps can be a discretional position, without being limited to average sensitivity G. Further, by varying gain set value G consecutively with rotating the gain knob by hand, it is possible to consecutively change the sensitivity range of the reflected echo signals to read out.

Embodiment 2

Figure 11:
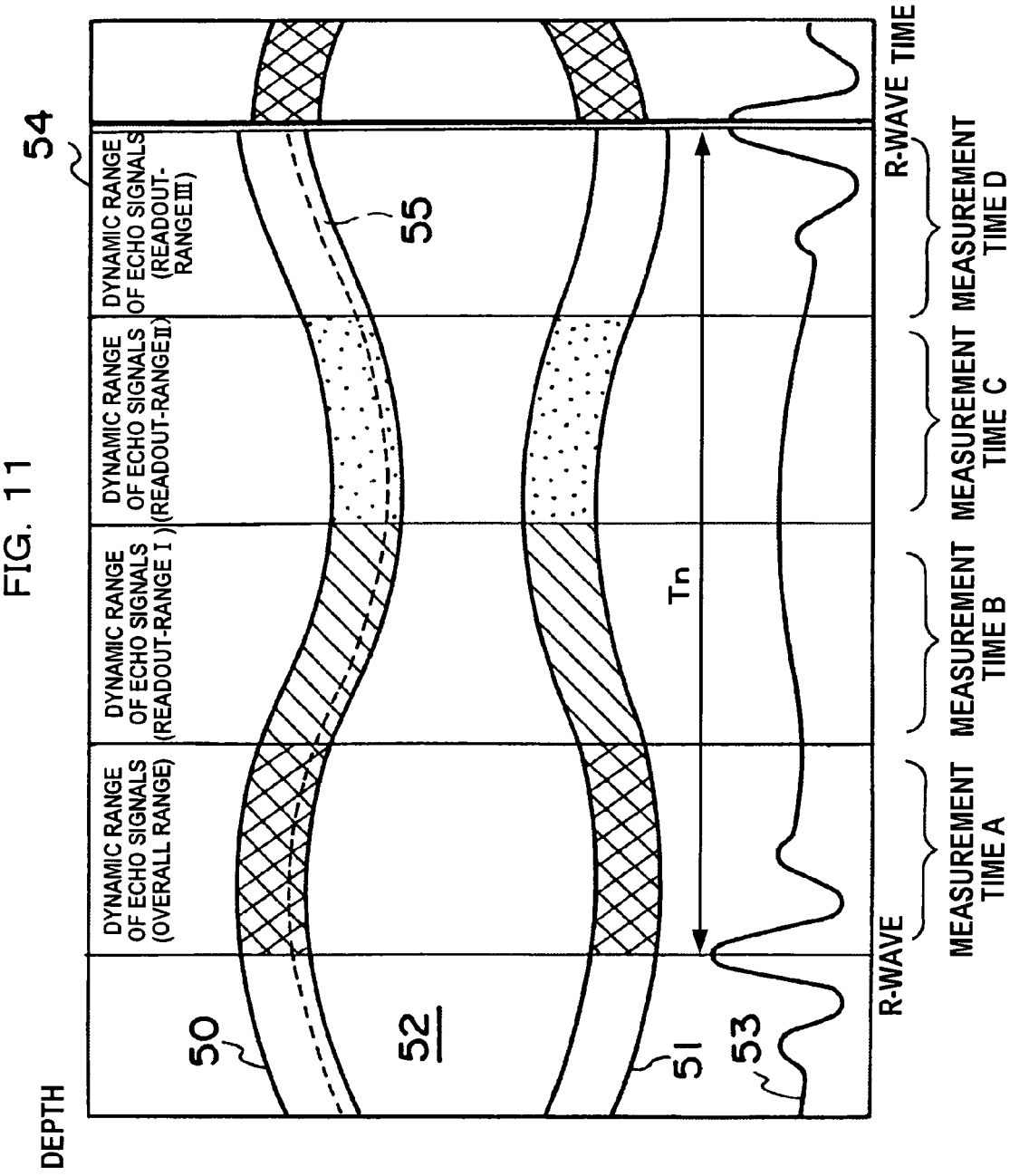
FIG. 11 is a diagram showing the M-mode images wherein the heartbeat cycles are broken up and displayed by varying the dynamic range on each time period.
Figure 12:
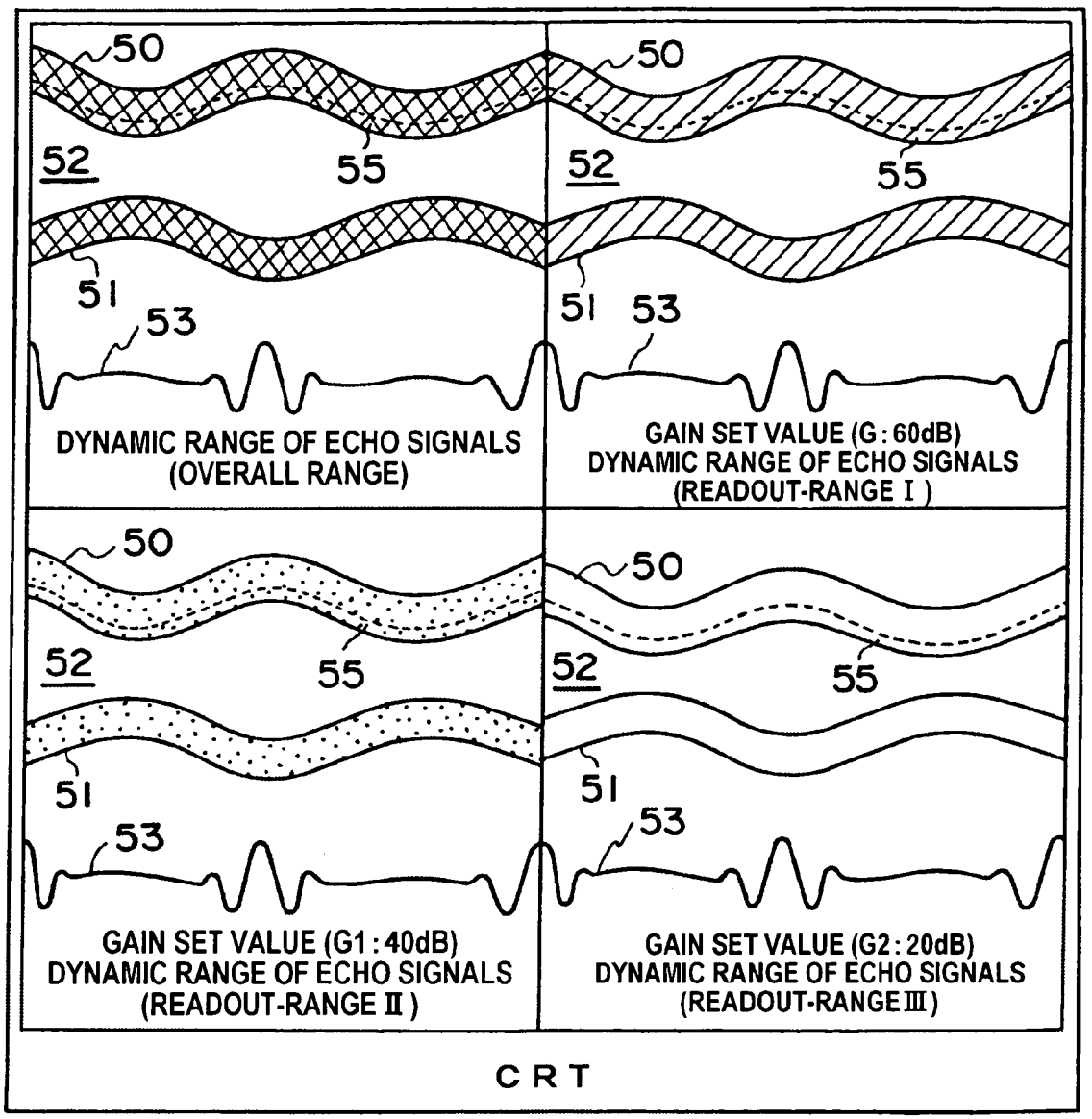
FIG. 12 is a diagram showing the display mode for displaying the plurality of M-mode images with different dynamic range on the monitor at the same time.

The second embodiment relating to the present invention will now be described referring to FIG. 11 and FIG. 12. The difference between the present embodiment and the first embodiment is that the intended ultrasound images are M-mode images, not B-mode images. In this embodiment, explanation will be omitted for the equivalent with embodiment 1 in function as well as configuration, with encoding remaining the same. FIG. 11 shows the M-mode images indicating the morphological variation of a heart wall in one heartbeat. FIG. 12 shows a display example of the plurality of M-mode images with different sensitivity range being arranged and displayed on the same screen simultaneously.

As shown in FIG. 11, M-mode images indicate temporal morphological variation toward ultrasound beam direction of, for example, heart wall 50 and 51 that form ventriculus sinister 52, and electrocardiographic (ECG) waveform 53 measured by an electrocadiograph (not shown in the diagram) is temporally synchronized with M-mode images and displayed. In this embodiment, one heartbeat cycle which is from R-wave to R-wave of ECG waveform 53 is set as a reference period, and measurement time A, measurement time B, measurement time C, and measurement time D are sequentially set as a measurement time wherein the one heartbeat cycle is segmented on plurality of different time. For setting the measurement times such as above, the plurality of ECG waveforms, for example, are measured in advance. Then the average of those heartbeat cycles are calculated in CPU 26 to find 1 heartbeat cycle Th. Measurement times A, B, C, and D (here D=Th−A+B+C) are set from the detection of R-wave, based on the above calculated heartbeat cycle Th.

Readout range-setting devices 34a, 34b, 34c, and 34d are incorporated with a software that designates which device should correspond to which measurement time, thus the operator can set the readout-range for the respective measurement time in dependence upon its function.

When the above setting is completed, the operator applies the probe on the chest region of the subject, and implements the B-mode measurement. Then upon obtaining the image that includes a section projecting the heart of the examinee at its best, the operator sets M-mode measurement direction to the B-mode image. And the M-mode measurement for one heartbeat is executed.

In the example shown in FIG. 11, in measurement time A, M-mode image is displayed according to the signals of the overall dynamic range as the sensitivity range in memory 18. This display mode is similar to the original image display of the B-mode images mentioned in embodiment 1. This display can be executed by reading out the data of the overall dynamic range, simply by turning on switch 34h, even upon executing with software processing.

Also, M-mode images are displayed, according to the readout range I (40~80 dB) in measurement time B, according to the readout range II (20~60 dB) in measurement time C, and according to the readout range III (0~40 dB) in measurement time D. In this way, the sensitivity range (dynamic range) of the echo signals read out from memory 18 with respect to each measurement time A-D can be automatically switched over.

In the mean time, as in the M-mode images of measurement time A, there are times, for example, when it is difficult to identify blood clot 55 formed in the inner heart wall 50 being buried by pedicardia fat. By the present embodiment, because the M-mode images are displayed according to the different echo signals based on the elapse of time, it is possible to display blood clog 55 on the B-mode image. In this embodiment, for example, in the B-mode image of measurement time D, it is easier to identify blood clog 55 comparing to the M-mode image of measurement time A, along with the elapse of time. Additionally, in this embodiment as M-mode display, a survey display mode which sequentially displays the measurement result by shifting rewriting line 54 from the left side to the right side is adopted, but a scroll display mode which displays the latest measurement result at all times also can be adopted.

The embodiment shown in FIG. 11 displays the period of one heartbeat with the plurality of sensitivity range, but it is also possible to arrange the plurality of M-mode images with different sensitivity range simultaneously on the same screen. This means enables the examiner to observe by comparing the respect M-mode images without looking away, thus makes it easier to determine, for example, blood clog 55. This example displays the respective M-mode images of two heartbeats, but this period of display only relates to how many cardiac cycles of M-mode images should be stored in memory 18, thus can be set at the discretion of the operator.

The ultrasonic diagnostic device relating to the present embodiment according to the first embodiment (the application mode for the B-mode) and the second embodiment (the application mode for the M-mode) have been described above, but the present invention also can be applied to Doppler mode (D-mode) and color flow mapping mode (CFM-mode).

Figure 13:
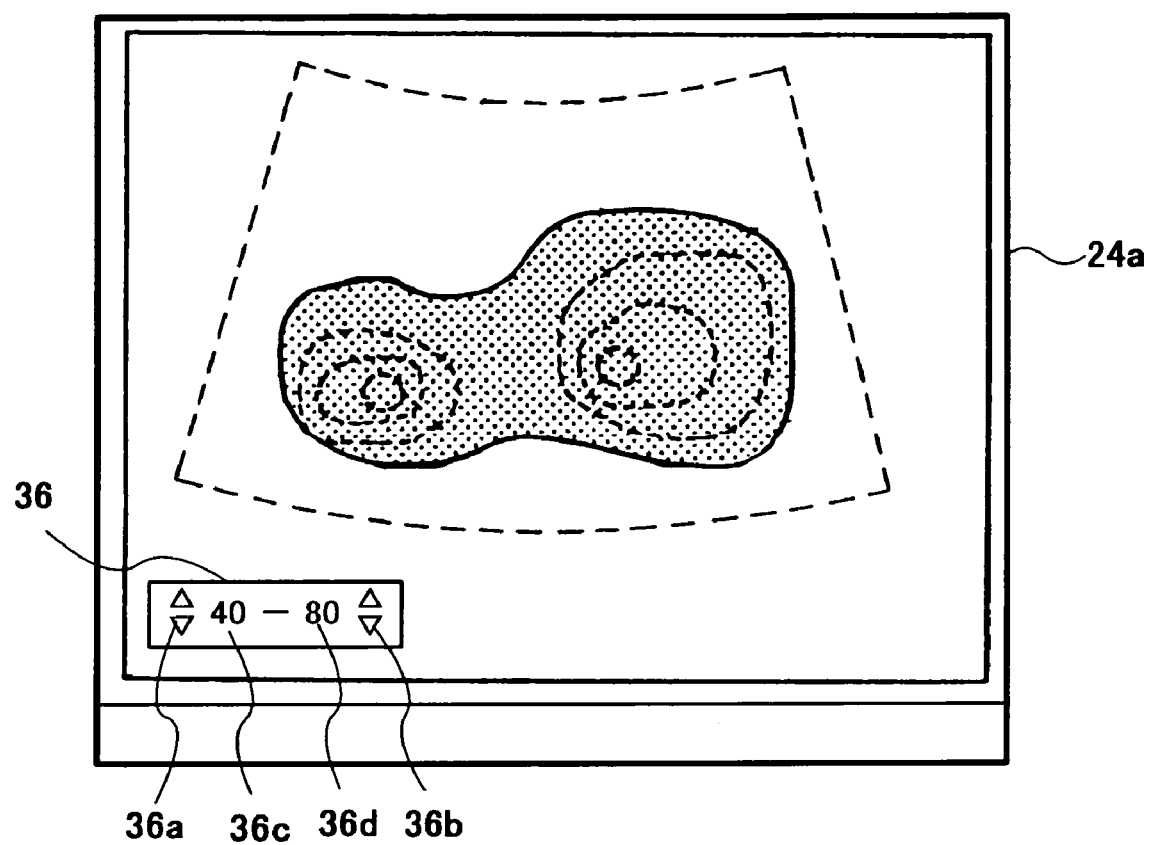
FIG. 13 is a diagram showing the other embodiment of the means for setting the readout-range of the echo signals stored in the memory.

The present invention can be applied further to a different embodiment. For example, in the first embodiment the example was described wherein the plurality of readout range-setting device 34 were incorporated into operation desk 28a, but the readout range-setting means can be configured with readout range-setting window 36 that is displayed on monitor 24a and an input device such as mouse 35 as shown in FIG. 13. In this case, in the readout range-setting window displayed on the monitor screen, arrow marks 36a and 36b that variably input the lower limit and the upper limit of the readout-range and digital readout unit 36c and 36d that display said range by numbers are provided. As for arrow marks 36a and 36b, upon clicking the arrow mark pointing upward with mouse 35 the range-setting value will be increased, and upon clicking the arrow mark pointing downward the range-setting value will be decreased. The numbers are varied in accordance with the clicking, as they are displayed on numerical display unit 36c and 36d. These numbers can be easily displayed by utilizing the character memory of the display unit. In addition, FIG. 13 exemplifies the display of one image, but in the case of displaying a plurality of images, the readout range-setting windows need to be provided in the display region of the respective images.

Also, as for the varied example of the present invention, after displaying the B-mode images with different sensitivity range, the color elastic images can be superposed on the B-mode images for display. Stated differently, as well as obtaining B-mode images with different sensitivity range, the color elastic images that indicate anatomic features such as hardness and softness of the diagnostic portions can be obtained. The color elastic images to be superposed and displayed with the respective B-mode images with different sensitivity range, are to be translucent by varying only the hue information out of YUV information of the color elastic images. By executing the above example, the sclerotic region caused by a tumor, for example, can be determined, and the fine structure of the anatomy can be viewed.

Also, upon displaying the B-mode images with different sensitivity range, it is preferable to display the numeric to represent the set sensitivity range (for example, the numeric to represent readout-range I, readout-range II and readout-range III) at the same time as displaying the B-mode images. This makes it easier to determine the next sensitivity range to be set, from the numeric that represents the displayed B-mode images and the sensitivity range. This means of display can be executed by utilizing the memories such as character memory or graphic memory provided in the ultrasonic diagnostic devices that display D-information or the examination information of the body of the object.

Moreover, in the present invention, it is possible to display the B-mode images with different sensitivity range and the M-mode images with different sensitivity range simultaneously on the same screen. In this case, it is preferable to have the measurement line of the M-mode written into the B-mode images. This makes it possible to determine the fine structure of the diagnostic portions (diaphragm, for example) by B-mode images, as well as to measure the temporal response of the mode of the diagnostic portions by M-mode images.

Also, the present invention can be arranged to have the means to create the interpolation data of the echo signals stored in memory 18. This makes it possible to display high-resolution ultrasound images by interpolation processing, even when the ultrasonic waves have few scanning lines.

Moreover, the present invention can be arranged to have an external main storage that stores the echo signals. This makes it possible, upon diagnosing the same diagnostic portion, to resume the ultrasonic diagnosis simply by reading out the echo signals from the external main storage.

As described above, by the present invention, it is possible to observe the anatomic features wherein the echo signals are in a narrow range with images of high-clarity.

The present invention also makes it possible to observe the anatomic features wherein the echo signals are in a narrow range with efficiency.

Moreover, the present invention enables the observing of the anatomic features wherein the echo signals are in a narrow range, without requiring advanced technique for regulating the devices.

The invention claimed is:

1. An ultrasonic diagnostic apparatus comprising:
    a probe that transmits ultrasound beams to the body of an object to be examined, as well as receives echo signals from said object;
    a reception unit that receives the echo signals from said probe;
    a storage means for storing the received echo signals;
    a readout-range setting means for setting at least two predetermined partial readout dynamic ranges which do not completely overlap one another for an overall dynamic range of the echo signals stored in said storage means;
    a means for reading out the echo signals of each of the at least two predetermined partial readout dynamic ranges set by said readout-range setting means, and for converting the readout signals of each of the at least two predetermined partial readout dynamic ranges to data having a display dynamic range of a display monitor; and
    a means for displaying each of the data converted by said data conversion means on the display monitor as an image.

2. The ultrasonic diagnostic apparatus according to claim 1, wherein said storage means is a memory that stores the receiving signals corresponding to one transmitted wave of said ultrasound beams, and a content of said memory is to be renewed every transmission/reception of the ultrasonic waves.

3. The ultrasonic diagnostic apparatus according to claim 1, wherein said storage means is a memory to store the echo signals obtained by scanning a cross-section of the body of the object one time by said ultrasound beams.

4. An ultrasonic diagnostic apparatus comprising:
    a probe that transmits ultrasonic beams to the body of an object to be examined, as well as receives the echo signals from said body of the subject;
    a reception unit that receives the echo signals from said probe;
    a storage means for storing the received echo signals;
    a readout-range setting means for setting a plurality of different partial readout dynamic ranges which do not completely overlap one another for an overall dynamic range of the echo signals stored in said storage means;
    a means for reading out the echo signals for each of the plurality of different readout dynamic ranges set by said readout range-setting means from said storage means, and for performing data conversion for each of the readout signals of the different dynamic ranges to data for a display of a dynamic range of a display monitor; and
    a means for creating image data for each data with the same readout dynamic range that is read out from the data converted by said data conversion means, and for displaying them on a monitor screen of the display monitor.

5. The ultrasonic diagnostic apparatus according to claim 4, wherein said plurality of different readout dynamic ranges is set by sequentially being switched over to said readout-range setting means, and the images that are displayed on said monitor is to be renewed every time said readout-range varies.

6. The ultrasonic diagnostic apparatus according to claim 5, wherein said plurality of readout dynamic ranges partially overlap.

7. The ultrasonic diagnostic apparatus according to claim 5, wherein said plurality of readout dynamic ranges are independent ranges with respect to one another.

8. The ultrasonic diagnostic apparatus according to claim 4, wherein said plurality of different readout dynamic ranges are set to said readout-range setting means simultaneously, and the plurality of the images are displayed on said monitor simultaneously.

9. The ultrasonic diagnostic apparatus according to claim 8, wherein said plurality of readout dynamic ranges partially overlap.

10. The ultrasonic diagnostic apparatus according to claim 8, wherein the plurality of readout dynamic ranges are independent ranges with respect to one another.

11. The ultrasonic diagnostic apparatus according to claim 5, wherein said readout-range setting means includes a means for reading out the data of the overall sensitivity range stored in said memory, and said data conversion means includes a means for converting data of an overall dynamic range into a display dynamic range of said monitor.

12. The ultrasonic diagnostic apparatus according to claim 4, wherein the images to be displayed on said monitor are one of B-mode images, H-mode images, P-mode images, or CFM images.

13. An ultrasonic diagnostic apparatus comprising:
a probe that transmits ultrasonic waves to the body of an object to be examined, as well as receives echo signals from said object;
a memory that stores the received echo signals for a portion of at least one image;
an image display means having a dynamic range for displaying B-mode images formed with the use of the echo signals of one image stored in said memory;
a means for setting a region of interest in the B-mode images displayed to said image display means;
a means for reading out the echo signals from said memory for at least two set partial dynamic ranges which do not completely overlap one another of an overall dynamic range of said memory corresponding to said region of interest;
a means for converting and outputting the echo signals for each of the at least two partial dynamic ranges read out from said memory to data; and
a means for forming image data from each of the data converted by said data conversion means, and for displaying them in the dynamic range of said image display means.

14. The ultrasonic diagnostic apparatus according to claim 13, wherein the images formed from the data of said at least two partial dynamic ranges are displayed independently.

15. The ultrasonic diagnostic apparatus according to claim 13, wherein the images formed from the data of said at least two partial dynamic ranges are composed with said B-mode images and displayed.

16. The ultrasonic diagnostic apparatus according to claim 15, wherein the images formed from the data of said at least two partial dynamic ranges are made by positioning and are also composed with said B-mode images to be displayed.

17. An ultrasonic diagnostic apparatus comprising:
a probe that transmits ultrasound beams to a body of an object to be examined, as well as receives echo signals from said object;
a reception unit that receives the echo signals from said probe;
an A/D conversion unit that converts the echo signals outputted from said reception unit into digital signals;
a digital phasing unit that executes phasing process on the outputted signals of said AID conversion unit, and forms reception beam signals;
a first memory that stores outputted signals of said digital phasing unit;
a readout-range setting device that sets at least two predetermined partial readout dynamic ranges which do not completely overlap one another for an overall dynamic range of the echo signals stored in said first memory;
a digital gain regulation circuit that reads out the echo signals of each of the at least two dynamic ranges set by said readout-range setting device, and performs data conversion of each of the read out signals to a display dynamic range of a display monitor; and
a second memory that forms image data with the use of data converted by said digital gain regulation circuit;
wherein said display monitor displays the image data formed in said second memory on a screen as images.

18. The ultrasonic diagnostic apparatus according to claim 17, wherein said first memory has a 3-demensional storage region consist of a scanning direction of the beams, a depth direction of the object of the beams, and a sensitivity direction of the echo signals.

19. The ultrasonic diagnostic apparatus according to claim 17, wherein said readout-range setting device is comprised of an operation device provided on a operating desk and an electric circuit that outputs the signals corresponding to operating quantity given to the operating device.

20. The ultrasonic diagnostic apparatus according to claim 17, wherein said readout-range setting device is comprised of a window that performs variable setting on the readout-dynamic range by an order that is displayed on said display monitor and is inputted from an input device, and an operating device that inputs the order to perform variable setting on said readout-dynamic range from said window.

21. The ultrasonic diagnostic apparatus according to claim 1, wherein said readout-range setting means sets three predetermined partial readout dynamic ranges to the overall dynamic range of the echo signals stored in said storage means.

22. The ultrasonic diagnostic apparatus according to claim 1, wherein said display means displays both of plural ultrasound images showing respective different readout dynamic ranges and the ultrasound image showing overall dynamic range of the received echo signals.

23. An ultrasonic diagnostic apparatus comprising:
a probe that transmits ultrasound beams to the body of an object to be examined, as well as receives echo signals from said object;
a reception unit that receives the echo signals from said probe;
a storage means for storing the received echo signals;
a readout-range dividing means for dividing an overall dynamic range of the echo signals stored in said storage means into at least two partial readout dynamic ranges which do not completely overlap one another; and
a means for displaying the echo signals of each partial readout dynamic range on a display monitor as an image having the display dynamic range.

* * * * *